United States Patent [19]

Kurono et al.

[11] Patent Number: 4,678,801
[45] Date of Patent: Jul. 7, 1987

[54] NOVEL 2-OXOPYRROLIDINE COMPOUNDS, SALTS THEREOF PROCESS FOR THE PREPARATION THEREOF AS WELL AS PHARMACEUTICAL AGENT COMPRISING THE COMPOUND

[75] Inventors: Masayasu Kurono, Mie; Motohide Hayashi, Kasugai; Tsunemasa Suzuki, Kumamoto; Kenji Miura, Kasugai; Yoshihiro Kumagai, Kasugai; Yukiharu Matsumoto, Kasugai; Seiji Miyano, Fukuoka; Kunihiro Sumoto, Ohnojo, all of Japan

[73] Assignee: Sanwa Kagaku Kenkyusho Co., Ltd., Aichi, Japan

[21] Appl. No.: 884,125

[22] Filed: Jul. 10, 1986

[30] Foreign Application Priority Data

Jul. 23, 1985 [JP] Japan ................... 60-161213

[51] Int. Cl.$^4$ ..................... A61K 31/40; C07D 487/06
[52] U.S. Cl. ..................... 514/413; 548/453
[58] Field of Search .................. 514/413; 548/453

[56] References Cited

U.S. PATENT DOCUMENTS 3,544,590 12/1970 Kittleson ........................ 548/453
4,564,624 1/1986 Miyano et al. .................. 514/413

FOREIGN PATENT DOCUMENTS 0083694 5/1983 Japan ................... 548/453

OTHER PUBLICATIONS

Noller, "Chemistry of Organic Compounds", 3rd. Ed., (1965), p. 268, [W. B. Saunders Ct., Phila. & London].

Primary Examiner—Joseph Paul Brust
Attorney, Agent, or Firm—Armstrong, Nikaido, Marmelstein & Kubovcik

[57] ABSTRACT

Novel 2-oxopyrrolidine compounds represented by the formula

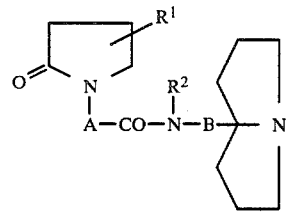

wherein $R^1$ and $R^2$ are hydrogen or alkyl group, respectively, A is alkylene group or phenyl substituted alkylene group, and B is alkylene group, or a salt thereof, a process for the preparation thereof, and a pharmaceutical agent comprising the compound or salt as an effective component.

14 Claims, No Drawings

NOVEL 2-OXOPYRROLIDINE COMPOUNDS, SALTS THEREOF PROCESS FOR THE PREPARATION THEREOF AS WELL AS PHARMACEUTICAL AGENT COMPRISING THE COMPOUND

BACKGROUND OF THE INVENTION

1. Field of the Invention

The present invention relates to novel 2-oxopyrrolidine compounds, or a salt thereof, a process for the preparation of the compound or salt as well as a pharmaceutical agent comprising at least one of the compound and salt to prevent or cure a cerebral dysfunction.

2. Related Arts

Hitherto, various studies have been made on γ-amino butyric acid (GABA) and its derivatives to seek for an effective component for curing a cerebral dysfunction. By the way of such studies, 2-oxo-1-pyrrolidineacetamide [Piracetam, 2-(pyrrolidin-2-on-1-yl)acetamide] has been discovered to draw a remarkable attention but higher pharmaceutical effects as initially expected have not been found thereon.

SUMMARY OF THE INVENTION

A primary object of the invention is to provide an effective agent for preventing or curing a cerebral dysfunction, which can be substituted for the Piracetam.

A secondary object of the invention is to provide an agent for preventing or curing the cerebral dysfunction, which shows a strong pharmaceutical action and no or quite low toxicity.

According to the invention, the above and other objects can be attained by a novel 2-oxopyrrolidine compound represented by the formula

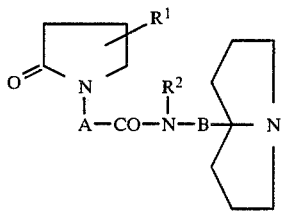

wherein $R^1$ and $R^2$ are hydrogen or alkyl group, respectively, A is alkylene group or phenyl substituted alkylene group, and B is alkylene group,
or a salt thereof.

Because the compounds (I) and salts thereof have an excellent cerebral metabolic activating action and cerebral function protecting action but show a quite low toxicity.

In the compounds of Formula (I), the term of "alkyl group" may be straight-chain alkyl radicals, branched-chain alkyl radicals or cycloalkyl radicals. As examples for the straight-chain alkyl radicals, one having 1 to 10 carbon atoms, for instance methyl, ethyl, n-propyl, n-butyl, n-pentyl, n-hexyl, n-decyl and the light may be listed. As examples for the branched-chain alkyl radicals, isopropyl, isobutyl, s-butyl, t-butyl, isopentyl and the like may be listed. As examples for the cycloalkyl radicals, cyclopropyl, cyclobutyl, cyclopentyl, cyclohexyl radicals and the like may be listed. The "alkylene group" may be straight-chain or branched chain alkylene radicals. As the straight-chain alkylene radicals, one having 1 to 3 carbon atoms, for instance methylene, ethylene, trimethylene may be listed. As the branched-chain alkylene radicals, one having 2 to 10 carbon atoms, for instance ethylidene, propylidene, butylidene, pentylidene, hexylidene, decylidene, isopropylidene, isobutylidene, isopentylidene, propylene, ethylethylene, ethyltrimethylene and the like may be listed.

The salts of the compound (I) are acid addition one having no toxicity. Such acids may be listed as one for forming the salt, as hydrogen chloride, hydrogen bromide or the like hydrogen halide, sulfuric acid, phosphoric acid or the like mineral acid, acetic acid, propionic acid, gluconic acid, maleic acid, fumaric acid, tartaric acid, succinic acid, lactic acid, benzoic acid, cinnamic acid or the like organocalboxylic acid, methanesulfonic acid or the like alkylsulfonic acid, p-toluenesulfonic acid or the like arylsulfonic acid, cyclohexyl-sulfonic acid or the like cycloalkylsulfonic acid, asparaginic acid, glutamic acid, N-acetylasparaginic acid, N-acetylglutamic acid or the like amino acid.

According to the process of the invention, the compounds (I) and salts thereof can be prepared by subjecting to react of a compound represented by the formula

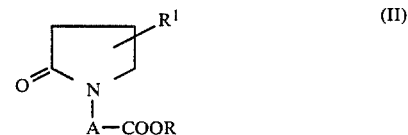

wherein $R^1$ and A have the meanings as referred to, and R is alkyl group,
with a compound represented by the formula

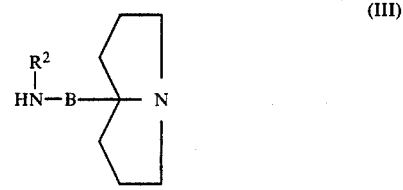

wherein $R^2$ and B have the meanings as referred to,
and if necessary, converting the resulting compound into the salt.

The reaction proceeds only with stirring the both raw materials in equimolar amount in the presence or absence of a solvent. As the solvent, toluene, xylene, N,N-dimethylformamide, N,N-dimethylacetamide or the like may be employed. A reaction temperature depends on a kind and other factors of the raw materials and solvent and thus it is not always constant but about 80° to 150° C. is preferable.

it is to be noted that each of the both raw materials can be prepared in a manner known per se. For instance, the raw materials shown by Formula (II) may be synthesized in accordance with the process as disclosed in Jap. Unexamined Patent Application Gazette No. 130656/1978, and the other raw materials shown by the Formula (III) may be synthesized in accordance with the process as disclosed in Jap. Unexamined Patent Application Gazette No. 156283/1981.

The compounds and salts according to the invention can be made into a medicine which comprises as an effective component at least one of the same. There is no limitation in form of the medicine and thus it may be made into a tablet, pill, hard capsule, soft capsule, powder, granule, suppository or the like solid drug, or solution, suspension, emulsion or the like liquid drug. In case for the solid drug, a starch, lactose, glucose, calcium phosphate, magnsium stearate, gum arabic or the like forming agent and if necessary, smoothening or greasing agent, binding agent, breaking agent, coating agent, coloring agent or the like may be added. In case for the liquid drug, a stabilizer, dissolving aid, suspending agent, emulsifying agent, buffering agent, storing agent or the like may be added.

A dosing amount of the compound or salt depends on various factors such as a kind of same, kind or state of a disease, age and state of a patient and others but for an adult, about 1 to 1000 mg/day and more particularly 5 to 30 mg/day is preferable.

The present invention has following advantages.

According to the process of the invention, the compounds and salts thereof can be prepared easily and with a relatively high yield by starting from the raw materials which are known per se or can easily be synthesized with use of known materials.

The compounds and salts thereof according to the invention are excellent in cerebral metabolic activating action and cerebral function protecting action and show a quite low toxicity, which mean that those are quite useful as an effective component for cerebral dysfunction curing or preventing agent. Therefore, the agent can be orally or non-orally dosed to patients with a senile dementia based on a primary cerebral degeneration, cerebral vascular dementia based on a cerebral vascular dysfunction and particularly cereblosclerosis, or a combined type dementia based on both of these factors. The compound or salt may be dosed to a study incompetent, amnesiac or patient with a clouding of consciousness based on an injury in head, for the purpose of appearance of activating action in central nervous system, or preventing such diseases.

PREFERRED EMBODIMENTS OF THE INVENTION

The invention will now be further explained with reference to Examples for manufacturing compounds and salts, Pharmacological Test Examples thereon and Examples for manufacturing pharmaceutical preparations.

Example 1

7a-(2-oxo-1-pyrrolidineacetamidomethyl)pyrrolizidine

A mixture consisting of 14.1 g (89.6 mmol) of methyl 2-oxo-1-pyrrolidineacetate and 11.4 g (81.4 mmol) of 7a-(aminomethyl)pyrrolizidine was heated and stirred for 6 hours at 80° C. under argon atmospher. After cooling, the reaction mixture was then solved with 1.0N-hydrochloric acid and extracted 3 times with dichloromethane. An aqueous layer was rendered alkaline by the addition of sodium hydroxide solution and extracted 3 times with dichloromethane followed by drying over anhydrous magnesium sulfate. After removal of the drying agent through filtration, the solvent was evaporated under reduced pressure to obtain a yellowish oil as a free base of the desired compound. The free base was converted to terephthalate by usual manner. Yield: 32.0 g (91.1%).

Terephthalate

Melting point: 193.2° C.

Elementary analysis: $C_{14}H_{23}N_3O_2 \cdot C_8H_6O_4$: Cal.: C, 61.24; H, 6.77; N, 9.74; Found: C, 61.19; H, 6.91; N, 9.58

IR spectrum $(\nu_{max}^{KBr})$ cm$^{-1}$: 1665, 1535, 1400

Mass spectrum (EI/DI) m/z: 166, 149, 110 (base peak)

Free base

NMR spectrum (CDCl$_3$) δ ppm:
1.07-3.17 (16H, m,

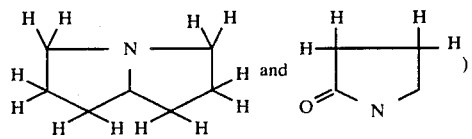

3.17 (2H, d, J=5.4 Hz,

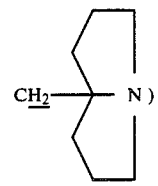

3.52 (2H, t, J=7.0 Hz,

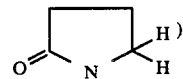

3.95 (2H, s,

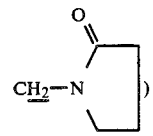

6.43-6.93 (1H, br, NH)

Examples 2 to 4

Following products were prepared with use of the conditions as described in Example 1.

(a) 7a-(2-oxo-1-pyrrolidineacetamidoethyl)pyrrolizidine

Picrate

Yield: 69.3%

Melting point: 168°-9° C.

Elementary analysis: $C_{15}H_{25}N_3O_2 \cdot C_6H_3N_3O_7$: Cal.: C, 49.60; H, 5.55; N, 16.53; Found: C, 49.51; H, 5.54; N, 16.53

IR spectrum $(\nu_{max}^{KBr})$ cm$^{-1}$: 1684, 1655, 1635, 1560, 1319

Mass spectrum (EI/DI) m/z: 279 (M+), 110 (base peak)

Free base

NMR spectrum (CDCl$_3$) δ ppm:
1.45-3.50 (20H, m,

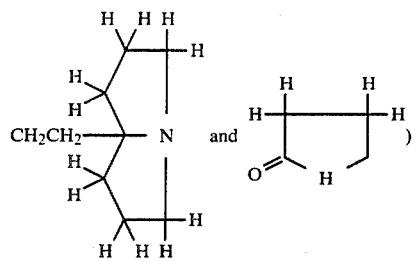

3.53 (2H, t, J=7.0 Hz,

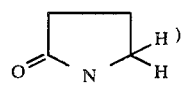

3.95 (2H, s,

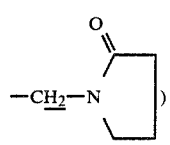

8.50–8.95 (1H, br, NH)

(b)
7a-[2-(2-oxo-1-pyrrolidine)butylamidomethyl]pyrrolizidine

Telephthalate

Yield: 69.3%
Melting point: 195°–7° C. (dec.)
Elementary analysis: $C_{16}H_{27}N_3O_2 \cdot C_8H_6O_4$: Cal.: C, 62.73; H, 7.24; N, 9.14; Found: C, 62.49; H, 7.41; N, 9.18
IR spectrum ($\nu_{max}^{KBr}$) cm$^{-1}$: 3262, 2890, 1671, 745
Mass spectrum (EI/DI) m/z: 166, 149, 110 (base peak)

Free base

NMR spectrum (CDCl$_3$) δ ppm:
0.90 (3H, t, J=7.0 Hz, —CH$_3$)
1.40–3.20 (18H, m,

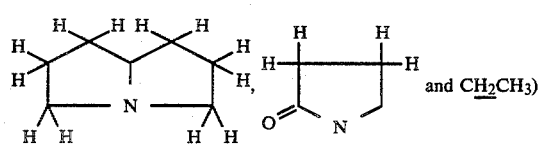

3.18 (2H, d, J=6.0 Hz,

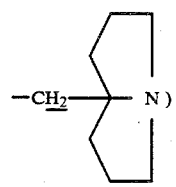

3.49 (2H, t, J=7.0 Hz,

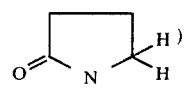

4.35–4.70 (1H, m,

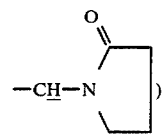

6.40–6.95 (1H, br, NH)

(c)
7a-[2-(2-oxo-1-pyrrolidinyl)-2-phenylacetamidomethyl]pyrrolizidine

Telephthalate

Yield: 83.0%
Melting point: 227°–9° C. (dec.)
Elementary analysis: $C_{20}H_{27}N_3O_2 \cdot 2/3 C_8H_6O_4$: Cal.: C, 67.28; H, 6.91; N, 9.29; Found: C, 62.23; H, 7.11; N, 9.33
IR spectrum ($\nu_{max}^{KBr}$) cm$^{-1}$: 3228, 1676, 1572, 1381, 1288, 812, 746
Mass spectrum (EI/DI) m/z: 110 (base peak)

Free base

Melting point: 110°–2° C.
NMR spectrum (CDCl$_3$) δ ppm:
1.30–4.05 (18H, m,

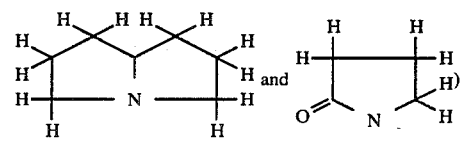

3.25 (2H, d, J=6.0 Hz,

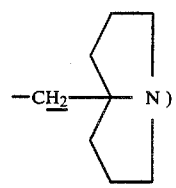

5.89 (1H, s,

—CH—Ph)

6.20–6.65 (1H, br, NH)
7.43 (5H, s, aromatic protons)

Example 5

7a-(5-methyl-2-oxo-1-pyrrolidineacetamidomethyl)pyrrolizidine

This compound was obtained with use of the condition as described in Example 1 and starting from methyl 5-methyl-2-oxo-1-pyrrolidineacetate instead of methyl 2-oxo-1-pyrrolidineacetate.

NMR spectrum (CDCl₃) δ ppm:
1.25 (3H, d, J=6.0 Hz, CH₃)
1.10–4.00 (17H, m,

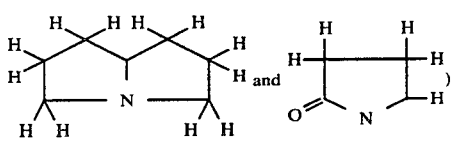

3.20 (2H, d, J=6.0 Hz,

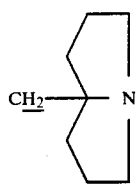

3.95 (2H, s,

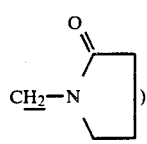

6.40–6.95 (1H, br, NH)

EXAMPLE 6

N-methyl-7a-(2-oxo-1-pyrrolidineacetamidomethyl)-pyrrolizidine

A mixture consisting of 1.60 g (10.2 mmol) of methyl 2-oxo-1-pyrrolidineacetate and 1.54 g (10.0 mmol) of 7a-methylaminomethylpyrrolizidine was heated and stirred for 3 hours at 140° to 150° C. under argon atmosphere and then the reaction mixture was treated in the manner as described in Example 1 to obtain the desired compound.

Yield: 2.17 g (77.8%)

IR spectrum $(v_{max}^{neat})$ cm⁻¹: 2950, 2860, 1690, 1660, 1465, 1290

Mass spectrum: (EI/DI) m/z; 110 (base peak); (CI/DI) m/z; 270 [(M+1)⁺, base peak]

NMR spectrum (CDCl₃) δ ppm:
1.30–4.90 (18H, m,

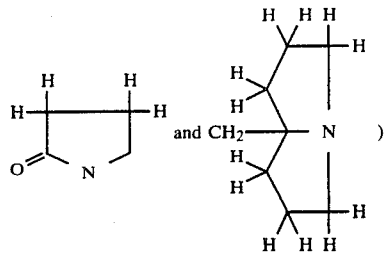

3.08 and 3.20 (3H, each s, N—CH₃)
3.55 (2H, t, J=7.0 Hz,

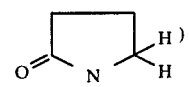

4.13 and 4.40 (2H, each s,

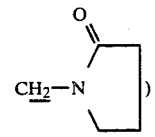

Pharmacological Test Example 1

(Effect on cerebral energy metabolism)

Cerebral metabolities were measured following bilateral common carotid artery occlusion in rats according to the method of Fujishima et al ["Rinsho to Kenkyu" (translated as—Clinic and Study—), Vol. 51, page 3532, 1974].

Spontaneously hypertensive male rats (SHR), each of which having weight of 250 to 350 g and having a blood pressure above 150 mmHg, were anesthetized with ether. The common carotid artery was exposed bilaterally and double ligated simultaneously. After 1 hour, a drug to be tested was orally administered and after having lapsed 5 hours from the administration, each of the animals was exposed to microwave (5.0 KW, 1.5 seconds). The cortex portion of brain was isolated and homogenated. Adenosin-tri-phosphate (ATP), glucose-6-phosphate (G-6-P), glucose, lactate and pyruvate concentrations in the tissue homogenate were determined by standard enzymatic methods.

As shown in following Table 1, it is suggested that the test compound (Example 1) improves cerebral energy metabolism in cerebral ischemia.

TABLE 1

| Test group | Dose (mg/kg) | Number of rat | A T P (μmol/g) | Lactic acid (L) (μmol/g) | Pyruvic acid (P) (μmol/g) | L/P ratio | G-6-P (μmol/g) | Glucose (μmol/g) |
|---|---|---|---|---|---|---|---|---|
| non-treatment | | 4 | 1.82 ± 0.04* | 1.94 ± 0.20*** | 390.9 ± 18.6* | 4.93 ± 0.40** | 169.52 ± 11.1 | 1.44 ± 0.05 |
| sham-operation | | 5 | 1.88 ± 0.02** | 1.80 ± 0.14** | 379.8 ± 8.2** | 4.75 ± 0.44** | 141.8 ± 4.6 | 1.54 ± 0.11 |
| control | | 4 | 0.70 ± 0.24 | 29.04 ± 2.01 | 543.7 ± 36.1 | 54.65 ± 26.99 | 114.8 ± 46.8 | 1.55 ± 0.69 |
| product of | 1 | 5 | 1.61 ± 0.32 | 14.36 ± 6.21 | 381.9 ± 124.4 | 30.64 ± 5.73* | 149.7 ± 11.1 | 2.78 ± 0.36 |
| Example 1 | 10 | 5 | 1.79 ± 0.13** | 9.01 ± 3.24** | 429.3 ± 77.3 | 22.15 ± 6.87* | 187.9 ± 10.9 | 3.40 ± 0.42* |
| Piracetam | 1 | 5 | 1.38 ± 0.34 | 20.35 ± 6.40 | 412.2 ± 95.0 | 44.53 ± 6.95 | 164.7 ± 26.7 | 2.41 ± 0.62 |

TABLE 1-continued

| Test group | Dose (mg/kg) | Number of rat | ATP (μmol/g) | Lactic acid (L) (μmol/g) | Pyruvic acid (P) (μmol/g) | L/P ratio | G-6-P (μmol/g) | Glucose (μmol/g) |
|---|---|---|---|---|---|---|---|---|
| | 10 | 6 | 1.37 ± 0.31 | 16.03 ± 5.26 | 341.0 ± 99.7 | 62.68 ± 29.78 | 155.0 ± 28.3 | 2.78 ± 0.80 |

Note
1: value is given as mean ± S.E.
2: Significantly difference from the control
*$P < 0.05$
**$P < 0.01$
***$P < 0.001$
3: Piracetam: 2-(pyrrolidin-2-on-1-yl)acetoamide Pharmaceutical Test Example 2

(Effect on gasping number after decapitation)

Cerebral protective effects of the compound according to the invention were examined in the complete ischemic model using the number of gasping of the decapitated head of mice, in accordance with the method of Holowach-Thurston J. et al ("Pediatr.", Vol. 8, Page 238, 1974).

Male ddY mice of 20 to 26 g were used. After having lapsed 30 minutes from an oral administration of the test compound, mice were decapitated and the number of gasping of the isolated heads were counted.

As shown in following Table 2, it is suggested that the test compound has the cerebral protective actions.

TABLE 2

| Test compounds | Dose | Number of mouse | Number of gasping |
|---|---|---|---|
| Non-treatment | | 10 | 5.0 ± 1.4 |
| Control | | 10 | 4.4 ± 1.0 |
| Product of Ex. 1 | 1 mg/kg p.o. | 10 | 5.9 ± 0.8 |
| | 10 mg/kg p.o. | 10 | 9.7 ± 1.3* |
| Piracetam | 1 mg/kg p.o. | 10 | 6.3 ± 1.4 |
| | 10 mg/kg p.o. | 10 | 7.0 ± 1.2 |
| | 100 mg/kg p.o. | 10 | 6.9 ± 1.2 |

Notes:
Values are given as mean ± S.E.,
Significantly different from the control, * $p < 0.01$, and
Piracetam: 2-(Pyrrolidin-2-on-1-yl)acetamide Pharmaceutical Test Example 3

(Effect on posttraumatic consciousness disturbance)

A cerebral protection from posttraumatic consciousness disturbance of mice was investigated by using the method of Manaka et al ("Igaku no Ayumi" (translated as—The Course of Medical Science—), Vol. 104, Page 253, 1978).

Male ddY mice having weight of 20 to 26 g were used. After having lapsed 30 minutes from oral administration of a test compound, the mice were fallen into a comatose state by dropping a stick (weight: 36 g) on the head from the hight of 40 cm. The time of appearance of righting reflex and spontaneous movement from this comatose state were measured.

As shown in following Table 3, it is suggested that the test compound has significant carebral protective effects in consciousness disturbance.

TABLE 3

| Test group | Dose (mg/kg) | Number of mouse | RRT (second) | SMT (second) |
|---|---|---|---|---|
| Control | | 17 | 132.8 ± 15.3 | 429.8 ± 39.3 |
| Product of Example 1 | 0.1 | 10 | 120.5 ± 13.8 | 443.2 ± 67.1 |
| | 1 | 15 | 100.1 ± 19.4 | 246.7 ± 38.7** |
| | 10 | 12 | 102.9 ± 24.6 | 253.4 ± 47.7** |
| Piracetam | 1 | 7 | 104.4 ± 17.4 | 387.4 ± 129.2 |

Note
1: Values are given as mean ± S.E.
2: Significantly different from the control, **$p < 0.01$
3: Piractam 2-(Pyrrolidin-2-on-1-yl)acetamide
4: RRT; Righting reflex time
SMT; Spontaneous movement time Pharmaceutical Test Example 4

(Acute toxicity)

A test compound was given to male ddY mice having weight of 19 to 23 g to observe an acute toxicity and weight change. Results are shown in following Table 4.

There was found neither case of death nor inhibition of weight increase. This means that a toxicity of the compound according to the invention is quite low.

TABLE 4

| | Dose (mg/kg) | Number of mouse | Weight 1st day | Weight 3rd day |
|---|---|---|---|---|
| Control | — | 10 | 21.0 ± 0.3 | 24.4 ± 0.3 |
| Product of Ex. 1 | 100 | 10 | 20.9 ± 0.3 | 24.6 ± 0.3 |
| | 1000 | 10 | 21.0 ± 0.3 | 24.4 ± 0.5 |

Pharmaceutical Agent Preparation Example 1

(Tablet)

120 g of the product according to Example 1 were mixed with 1000 g of lactose and 48 g of hydroxypropylcellulose. The mixture was granuled with use of aqueous solution of ethanol (ethanol:water=50:50), dried and screened. The resulting granules were mixed with 34 g of corn starch and punched in a conventional manner to obtain 6000 tablets, each containing 20 mg of the compound.

If necessary, the tablets can be made into film or sugar coated one, in a conventional manner.

Pharmacological Agent Preparation Example 2

(Capsule)

| Component | Amount |
|---|---|
| Product of Example 1 | 200 (g) |
| Lactose | 1470 |
| Magnesium stearate | 30 |

The components were mixed. The resulting powder mixture was charged in each hard gelatin capsule, so as to contain the mixture in 170 mg and to obtain 10000 capsules, each of which contains 20 mg of the compound.

Pharmaceutical Agent Preparation Example 3

(Granule)

| Component | Amount |
|---|---|
| Product of Example 1 | 400 (g) |
| Hydroxypropylcellulose | 200 |
| Corn starch | 3380 |
| Lactose | 6000 |
| Magnesium stearate | 20 |

The components were mixed and treated in a conventional manner to obtain 10 kg of granules which were packed separately, each containing 0.5 g of the granules (each package contains 20 mg of the compound).

Pharmaceutical Agent Preparation Example 4

(Injection)

An injection was prepared in a conventional manner under the following prescription.

| Component | Amount |
|---|---|
| Product of Example 1 | 100 mg |
| Polyethylene glycol | 2 ml |
| Distilled water | remainder |
| (total) | 5 ml/vial |

Pharmaceutical Agent Preparation Example 5

(Injection)

An injection was prepared in a conventional manner under the following prescription.

| Component | Amount |
|---|---|
| Product of Example 1 | 100 mg |
| Sodium acetate | 2 mg |
| Acetic acid (to control pH to 5.8) | suitable amount |
| Distilled water | remainder |
| (total) | 5 ml/vial |

We claim:

1. A 2-oxopyrrolidine compound represented by the formula

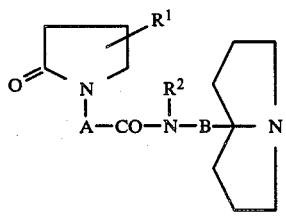

(I)

wherein $R^1$ and $R^2$ are independently hydrogen, straight-chain alkyl of 1-10 carbon atoms, branched-chain alkyl of 3-5 carbon atoms, or cycloalkyl of 3-6 carbon atoms, A is straight-chain alkylene of 1-3 carbon atoms; branched-chain alkylene of 2-10 carbon atoms, each of said alkylene being unsubstituted or substituted with a phenyl group, and B is straight-chain alkylene of 1-3 carbon atoms or branched-chain alkylene of 2-10 carbon atoms, or a non-toxic acid-addition salt thereof.

2. A compound and salt as claimed in claim 1, wherein said compound is 7a-(2-oxo-1-pyrrolidineacetamidomethyl)pyrrolizidine.

3. A compound and salt as claimed in claim 1, wherein said compound is 7a-(2-oxo-1-pyrrolidineacetamidoethyl)pyrrolizidine.

4. A compound and salt as claimed in claim 1, wherein said compound is 7a-[2-(2-oxo-1-pyrrolidine)-butylamidomethyl]pyrrolizidine.

5. A compound and salt as claimed in claim 1, wherein said compound is 7a-[2-(2-oxo-1-pyrrolidine)-2-phenylacetamidomethyl]pyrrolizidine.

6. A compound and salt as claimed in claim 1, wherein said compound is 7a-(5-methyl-2-oxo-1-pyrrolidineacetamidomethyl)pyrrolizidine.

7. A compound and salt as claimed in claim 1, wherein said compound is N-methyl-7a-(2-oxo-1-pyrrolidineacetamidomethyl)pyrrolizidine.

8. An agent for preventing and curing a cerebral dysfunction, which comprises, as an effective component, a cerebral dysfunction preventing amount of at least one 2-oxopyrrolidine compound represented by the formula

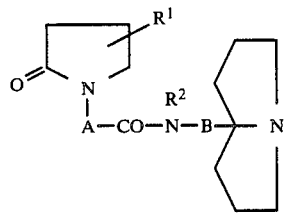

wherein $R^1$ and $R^2$ are independently hydrogen, straight-chain alkyl of 1-10 carbon atoms, branched-chain alkyl of 3-5 carbon atoms, or cycloalkyl of 3-6 carbon atoms, A is straight-chain alkylene of 1-3 carbon atoms; branched-chain alkylene of 2-10 carbon atoms, each of said alkylene being unsubstituted or substituted with a phenyl group, and B is straight-chain alkylene of 1-3 carbon atoms or branched-chain alkylene of 2-10 carbon atoms, or a pharmaceutically acceptable non-toxic acid-addition salt thereof and a pharmaceutically acceptable diluent.

9. An agent as claimed in claim 8, wherein said effective component is selected from the group consisting of 7a-(2-oxo-1-pyrrolidineacetamidomethyl)pyrrolizidine and said pharmaceutically acceptable salts thereof.

10. An agent as claimed in claim 8, wherein said effective component is selected from the group consisting of 7a-(2-oxo-1-pyrrolidineacetamidoethyl)pyrrolizidine and said pharmaceutically acceptable salts thereof.

11. An agent as claimed in claim 8, wherein said effective component is selected from the group consisting of 7a-[2-(2-oxo-1-pyrrolidine)butylamidomethyl]pyrrolizidine and said pharmaceutically acceptable salts thereof.

12. An agent as claimed in claim 8, wherein said effective component is selected from the group consisting of 7a-[2-(2-oxo-1-pyrrolidine)-2-phenylacetamidomethyl]-pyrrolizidine and said pharmaceutically acceptable salts thereof.

13. An agent as claimed in claim 8, wherein said effective component is selected from the group consisting of 7a-(5-methyl-2-oxo-1-pyrrolidineacetamidomethyl)pyrrolizidine and said pharmaceutically acceptable salts thereof.

14. An agent as claimed in claim 8, wherein said effective component is selected from the group consisting of N-methyl-7a-(2-oxo-1-pyrrolidineacetamidomethyl)-pyrrolizidine and said pharmaceutically acceptable salts thereof.

* * * * *